United States Patent [19]

James et al.

[11] Patent Number: 4,693,875

[45] Date of Patent: Sep. 15, 1987

[54] PROCESS FOR RECOVERY OF HYDROGEN AND ABSTRACTION OF SULFUR

[75] Inventors: Brian R. James; Chung Li-Lee, both of Vancouver, Canada; Michael A. Lilga; David A. Nelson, both of Richland, Wash.

[73] Assignee: Battelle Memorial Institute, Richland, Wash.

[21] Appl. No.: 900,863

[22] Filed: Aug. 27, 1986

[51] Int. Cl.$^4$ ............................................. C01B 17/05
[52] U.S. Cl. ................................... 423/243; 423/539; 423/648 R; 556/18
[58] Field of Search ............. 556/18; 423/243, 648 R, 423/539

[56] References Cited

U.S. PATENT DOCUMENTS

| | | | |
|---|---|---|---|
| 3,632,824 | 1/1972 | Fitton et al. | 556/18 |
| 4,097,509 | 6/1978 | Schmidbauer et al. | 556/18 |
| 4,283,373 | 8/1981 | Frech et al. | 423/243 |
| 4,532,116 | 7/1985 | Doerges et al. | 423/243 |
| 4,536,381 | 8/1985 | Blytas | 423/243 |
| 4,592,905 | 6/1986 | Plummer et al. | 423/648 R |

OTHER PUBLICATIONS

A. L. Balch, L. S. Benner, and M. M. Olmstead, *Inorg. Chem.*, 1979, 18, 2996.
C. L. Lee, B. R. James, D. A. Nelson, and R. T. Hallen, *Organometallics*, 1984, 3, 1360.

*Primary Examiner*—John Doll
*Assistant Examiner*—Wayne A. Langel
*Attorney, Agent, or Firm*—Benjamin Mieliulis

[57] ABSTRACT

A process of abstracting sulfur from $H_2S$ and generating hydrogen is disclosed comprising dissolving $Pd_2X_2(\mu\text{-dppm})_2$ in a solvent and then introducing $H_2S$. The palladium complex abstracts sulfur, forming hydrogen and a ($\mu$-S) complex. The ($\mu$-S) complex is readily oxidizable to a ($\mu$-$SO_2$) adduct which spontaneously loses $SO_2$ and regenerates the palladium complex.

6 Claims, No Drawings

PROCESS FOR RECOVERY OF HYDROGEN AND ABSTRACTION OF SULFUR

BACKGROUND OF THE INVENTION

1. Field of the Invention

This invention relates to the interaction of transition metal complexes, more specifically, palladium complexes with $H_2S$. More particularly, this invention discloses a process for removing $H_2S$ from a feedstock such as natural gas by means of a palladium metal-metal bonded dimer that abstracts the sulfur and generates hydrogen.

Field natural gas typically contains undesirable constituents such as $H_2S$ which must be removed because of its corrosive and noxious nature. $H_2S$ is now removed by treatment with aqueous ethanolamine in a countercurrent cycle followed by regeneration in a stripper column. Amines are often used and typical amines used are diisopropylamine or methyldiethanolamine. B,B'-hydroxyaminoethyl ether known as diglycolamine is also sometimes used.

The preferred alkanolamines typically have a hydroxyl group to lower the vapor pressure and to provide water solubility. The alkaline amine group absorbs acidic contaminant gases.

The alkanolamines, however, suffer several drawbacks—a problematic and costly one being the formation of irreversible reaction products with some contaminants such as COS and $CS_2$. This results in an economic loss from loss of alkanolamine if these contaminants are present in the well. Other drawbacks of alkanolamines include relatively high corrosivity, vaporization losses due to their relatively high vapor pressure, and the need often to keep water content below 5% which necessitates high reboiler temperatures.

A sweetening process for soured natural gas, able to effectively remove $H_2S$ but without many of the above attendant drawbacks, would be an advance in the art.

2. Description of Related Art

The palladium dimer complexes $Pd_2Cl_2(\mu\text{-dppm})_2$ have been reported by A. L. Balch, L. S. Benner, and M. M. Olmstead, *Inorg. Chem.*, 1979, 18, 2996 and C. L. Lee, B. R. James, D. A. Nelson, and R. T. Hallen, *Organometallics*, 1984, 3, 1360.

The present invention discloses a new and useful process utilizing these complexes.

SUMMARY OF THE INVENTION

This invention discloses a process for the removal of $H_2S$ from a gas feedstock and the conversion of the $H_2S$ to hydrogen and organosulfur compounds.

The invention is based on the discovery of the reaction:

$$\begin{array}{c}\text{CH}_2\\ \text{Ph}_2\text{P}\diagup\ \ \diagdown\text{PPH}_2\\ |\ \ \ \ \ \ \ \ \ \ |\\ \text{X}-\text{Pd}-\!\!-\!\!-\!\!-\text{Pd}-\text{X}\\ |\ \ \ \ \ \ \ \ \ \ |\\ \text{Ph}_2\text{P}\diagdown\ \ \diagup\text{PPh}_2\\ \text{CH}_2\end{array} + H_2S \longrightarrow \begin{array}{c}\text{CH}_2\\ \text{Ph}_2\text{P}\diagup\ \ \diagdown\text{PPh}_2\\ |\ \ \ \text{S}\ \ \ |\\ \text{Pd}\diagup\ \diagdown\text{Pd}\\ \text{X}\diagup|\ \ \ \ \ |\diagdown\text{X}\\ \text{Ph}_2\text{P}\diagdown\ \ \diagup\text{PPh}_2\\ \text{CH}_2\end{array} + H_2$$

(1a)  (1b)

where $X = Cl$, $Br$, or $I$.

The palladium complex (1a) is $[Pd_2X_2(\mu\text{-dppm})_2]$, where dppm is bis(diphenylphosphino)methane and X is Cl, Br, or I. The complex (1a) is a bridged dppm dimer, $[Pd_2X_2(\mu\text{-dppm})_2]$, but is written for convenience as $Pd_2X_2(dppm)_2$. All of the above are to be understood herein and are defined herein as equivalent representations of the same palladium complex.

This reaction can be carried out in solution under ambient conditions. Therefore, $Pd_2Cl_2(dppm)_2$ can be used to remove $H_2S$ from soured natural gases.

It has been found that $H_2S$ can be removed from natural gases by bubbling the gas through a $CH_2Cl_2$ solution of $Pd_2Cl_2(dppm)_2$ at $10^{-1}\text{-}10^{-2}$M. The palladium complex abstracts sulfur with the concomitant release of hydrogen. The sulfur-bearing palladium complex then can be oxidized with a mild oxidant to an $SO_2$ containing product, $Pd_2Cl_2(\mu\text{-dppm})_2(\mu\text{-SO}_2)$, that spontaneously releases the $SO_2$ with regeneration of the palladium complex.

DETAILED DESCRIPTION

When $Pd_2Cl_2(dppm)_2$ is dissolved in a solvent such as dichloromethane and exposed to $H_2S$, $Pd_2Cl_2(dppm)_2(\mu\text{-S})$ is formed together with the evolution of hydrogen gas. Essentially, hydrogen is split from the $H_2S$ molecule and sulfur is incorporated between the two palladium atoms. The reaction can be written as $Pd_2Cl_2(dppm)_2 + H_2S \rightarrow Pd_2Cl_2(dppm)_2(\mu\text{-S}) + H_2$ or in general as:

$$\begin{array}{c}\diagup\ \ \diagdown\\ \text{P}\ \ \ \ \ \ \text{P}\\ |\ \ \ \ \ \ \ |\\ \text{X}-\text{Pd}\ \ \ \ \text{Pd}-\text{X}\\ |\ \ \ \ \ \ \ |\\ \text{P}\ \ \ \ \ \ \text{P}\\ \diagdown\ \ \diagup\end{array} + H_2S \longrightarrow \begin{array}{c}\diagup\ \ \diagdown\\ \text{P}\ \ \ \ \ \ \text{P}\\ |\ \ \text{S}\ \ |\\ \text{Pd}\diagup\ \diagdown\text{Pd}\\ \text{X}\diagup|\ \ \ \ |\diagdown\text{X}\\ \text{P}\ \ \ \ \ \ \text{P}\\ \diagdown\ \ \diagup\end{array} + H_2$$

wherein P⌒P is bis(diphenylphosphino)methane, and X is selected from Cl, Br or I.

Quantitative measurements show that 97% of the theoretical amount of hydrogen is obtained.

The relative reactivities toward $H_2S$ of the differing halogen substituents are:

$Pd_2Cl_2(dppm)_2 > Pd_2Br_2(dppm)_2 > Pd_2I_2(dppm)_2$.

$Pd_2Br_2(dppm)_2$ reacts considerably slower than $Pd_2Cl_2(dppm)_2$, and the iodo substituted complex slower still.

The commercial significance of the $Pd_2Cl_2(dppm)_2$ route to hydrogen generation becomes apparent upon the recognition that $Pd_2Cl_2(dppm)_2$ can be regenerated from $Pd_2Cl_2(dppm)_2(\mu\text{-S})$ by oxidizing the sulfur to $SO_2$. The complex thus becomes valuable for the quantitative recovery of hydrogen from $H_2S$.

A one step hydrogen separation and sulfur abstraction from gas mixtures with compositions similar to that of oxygen blown coal gas is made possible by the invention. Quite generally it can be stated that $Pd_2X_2(dppm)_2(\mu\text{-SO}_2)$ can be generated from $Pd_2X_2(dppm)_2(\mu\text{-S})$ by oxidation wherein X=Cl or Br or I. Oxidation can be carried out using oxidants such as $H_2O_2$, pyridinium chlorochromate, pyridinium dichromate, and m-chloroperbenzoic acid. The $SO_2$ adduct is formed in high yields when the oxidation is performed at $-20°$ C. with two equivalents of oxidant. Oxidation of $Pd_2Cl_2(dppm)_2(\mu\text{-S})$ with a slight excess of m-chloroperbenzoic acid at $-20°$ C. followed by addition of hydrazine to element excess oxidant resulted in the formation of $Pd_2Cl_2(dppm)_2(\mu\text{-SO}_2)$ in 76% isolated yield.

Though the $SO_2$ adduct tends to spontaneously lose $SO_2$ thus regenerating the $Pd_2X_2(dppm)_2$ catalyst, the rate and extent of regeneration of the $Pd_2X_2(dppm)_2$ catalyst can be maximized or enhanced by using means removing SO$_2$ from the SO$_2$ adduct. The removal means to liberate SO$_2$ can be selected from N$_2$ gas introduction, application of heat, or application of reduced pressure.

The violet Pd$_2$X$_2$(dppm)$_2$($\mu$-SO$_2$) (X=Cl, Br, I) complexes lose SO$_2$ when N$_2$ is bubbled through the solution or if subjected to heat or vacuum. The rate of SO$_2$ loss decreases in the order to I>Br>Cl as judged by color change in samples of similar concentration.

TABLE 1

PHYSICAL PROPERTIES OF SOLVENTS FOR DISSOLUTION OF Pd$_2$Cl$_2$(dppm)$_2$

| Solvent | Solubility Parameter | Vapor Pressure at 25° C. (torr) | Boiling Point (°C.) |
|---|---|---|---|
| dichloromethane | 9.80 | 424 | 39.7 |
| dimethylacetamide | 10.80 | ~0 | 165 |
| diphenylether | 10.10 | 0.10 | 258 |
| 1,2,3,4-tetrahydro-naphthalene(tetralin) | 9.50 | 0.38 | 205 |
| dibutylphthalate | 9.85 | ~0 | 340 |
| 1,1,2-trichloroethane | 9.88 | 22.49 | 113.8 |
| 1,2,3-trichloropropane | 10.09 | 3.33 | 156 |

Pd$_2$Cl$_2$(dppm)$_2$ has a solubility of 0.15M in trichloroethane and 0.027M in trichloropropane.

Solvent choice appears to have an effect on the lifetime of the complex in solution.

Pd$_2$Cl$_2$(dppm)$_2$ is soluble in dichloromethane to form a 0.05M solution. The boiling point (39.7° C.) and vapor pressure (424 torr at 25° C.) of dichloromethane however do not make it the easiest solvent to work with.

Solvents more suitable for dissolution of Pd$_2$Cl$_2$(dppm)$_2$ can be determined by the concept of solubility parameters as illustrated by Hildebrand, J., and Scott, R. L. *The Solubility of Nonelectrolytes*, 3rd Ed., Reinhold Publishing Corp., New York, 1950, and Hoy, K. L. *J. Paint Technol.*, 42, 1, 1970.

The solubility parameter ($\delta$) is related to the internal pressure or cohesive energy density $\delta = (\Delta E/V)$ where $\Delta E$=energy of vaporization and
V=molar volume.

The solubility parameter of Pd$_2$Cl$_2$(dppm)$_2$ is estimated as approximately 10 based on its solubility in dichloromethane.

Possible process solvents can be tetralin [though its UV/VIS spectrum overlaps somewhat with that of Pd$_2$Cl$_2$(dppm)$_2$], dibutylphthalate, or diphenylether. Table 1 lists several possible solvents. Based on costs, 1,1,2-trichloroethane was preferred for Pd$_2$X$_2$(dppm)$_2$, where X=Cl or Br.

The projected economics for hydrogen separation by the process of the invention are dependent on the lifetime of the palladium catalyst in solution. Complex lifetime appears influenced by the solvent selected. Laboratory experience with trichloroethane as solvent seemed to suggest that the complex longevity in trichloroethane might be less than optimum in some commercial operations. More favorable complex lifetimes were found with dichloromethane solvent.

The principles, preferred embodiments, and modes of operation of the present invention have been described in the foregoing specification. The invention which is intended to be protected herein, however, is not to be construed as limited solely to the specific structure and formulas disclosed, since these are to be regarded as illustrative rather than restrictive. Variations and changes can be made by those skilled in the art without departing from the spirit and scope of the invention.

We claim:

1. A process for abstracting sulfur and forming hydrogen comprising:
   dissolving in a solvent a palladium complex of the formula, Pd$_2$X$_2$($\mu$-dppm)$_2$,
   wherein dppm=bis(diphenylphosphino)methane,
   wherein X is selected from Cl, Br, or I,
   introducing H$_2$S to the palladium complex in solution whereby sulfur is abstracted by the complex from the H$_2$S to form Pd$_2$X$_2$($\mu$-S)($\mu$-dppm)$_2$ and hydrogen.

2. The process according to claim 1 comprising the additional step of oxidizing the Pd$_2$X$_2$($\mu$-S)($\mu$-dppm)$_2$ to form a ($\mu$-SO$_2$) complex of the formula Pd$_2$X$_2$($\mu$-SO$_2$)($\mu$-dppm)$_2$, whereby the ($\mu$-SO$_2$) complex spontaneously loses SO$_2$ to regenerate the palladium complex.

3. The process according to claim 2 comprising in addition the step of:
   introducing N$_2$ gas to the ($\mu$-SO$_2$) complex to facilitate the loss of SO$_2$ to regenerate the palladium catalyst.

4. A process for abstracting sulfur from an H$_2$S containing gas and forming hydrogen comprising establishing a palladium complex of the formula

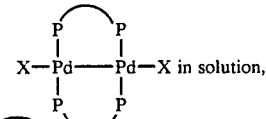

wherein P⌒P=bis(diphenylphosphino)methane,
wherein X is selected from Cl, Br, or I,
   introducing H$_2$S to the palladium complex in solution,
   reacting the palladium complex with the H$_2$S according to the reaction

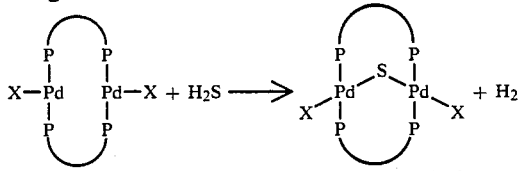

whereby sulfur is abstracted and hydrogen is formed.

5. The process according to claim 4 comprising the additional step of oxidizing the

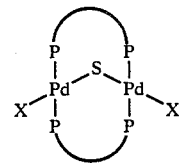

by exposure to an oxidant to form an SO$_2$ adduct, the SO$_2$ adduct tending to spontaneously lose SO$_2$ to regenerate the palladium complex.

6. The process according to claim 5 comprising in addition the step of regenerating the palladium complex by removal means causing the SO$_2$ adduct to lose SO$_2$, the removal means selected from introducing N$_2$ gas, applying heat, or applying reduced pressure.

* * * * *

UNITED STATES PATENT AND TRADEMARK OFFICE
CERTIFICATE OF CORRECTION

PATENT NO. : 4,693,875
DATED : September 15, 1987
INVENTOR(S) : Brian R. James, Chung Li-Lee; Michael Lilga and David Nelson It is certified that error appears in the above—identified patent and that said Letters Patent is hereby corrected as shown below:

Column 1, Line 5, before the heading "BACKGROUND OF THE INVENTION" add the following paragraph:

"This invention was made with government support under Contract No. DE-AC06-76RLO 1830 awarded by the U.S. Department of Energy. The government has certain rights in the invention."

Signed and Sealed this

Nineteenth Day of December, 1989

Attest:

JEFFREY M. SAMUELS

Attesting Officer    Acting Commissioner of Patents and Trademarks